United States Patent
Gupte et al.

(10) Patent No.: US 12,336,909 B2
(45) Date of Patent: Jun. 24, 2025

(54) BIASED CAPSULE FOR TRANSCATHETER VALVE REPAIR AND METHODS

(71) Applicant: Medtronic, Inc., Minneapolis, MN (US)

(72) Inventors: Kimaya N. Gupte, Santa Rosa, CA (US); Christina E. Franke, Santa Rosa, CA (US); Alexandra C. Dotti, Santa Rosa, CA (US); Isabel H. Mulvihill, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 582 days.

(21) Appl. No.: 17/590,328

(22) Filed: Feb. 1, 2022

(65) Prior Publication Data

US 2022/0280293 A1 Sep. 8, 2022

Related U.S. Application Data

(60) Provisional application No. 63/157,202, filed on Mar. 5, 2021.

(51) Int. Cl.
*A61F 2/24* (2006.01)
*A61F 2/95* (2013.01)
(Continued)

(52) U.S. Cl.
CPC .......... *A61F 2/2436* (2013.01); *A61F 2/2418* (2013.01); *A61F 2/9517* (2020.05);
(Continued)

(58) Field of Classification Search
CPC .... A61F 2/2436; A61F 2/2418; A61F 2/9517; A61F 2/9661; A61F 2002/9623;
(Continued)

(56) References Cited

U.S. PATENT DOCUMENTS

| 7,803,185 B2 | 9/2010 | Gabbay |
| 8,518,098 B2 | 8/2013 | Roeder et al. |

(Continued)

FOREIGN PATENT DOCUMENTS

WO 2016/176610 A1 11/2016

OTHER PUBLICATIONS

Extended European Search Report, EP Application No. 22158962.5, dated Oct. 17, 2022.
(Continued)

*Primary Examiner* — Jerrah Edwards
*Assistant Examiner* — Jose H. Trevino, III

(57) ABSTRACT

Aspects of the disclosure include delivery devices for transcatheter delivery of a cardiac implant. Delivery devices can include a handle assembly as well as a piston mount connected to the handle assembly and having a distal portion terminating at a nose cap. The distal portion includes a stop extending radially from and fixed to the distal portion. The delivery device further includes a capsule assembly including a biasing element for selectively sheathing the implant and a plurality of retraction members secured about a distal end of the biasing element to control deployment of the implant. In various examples, the biasing element is a helical compression spring and the implant is a prosthetic tricuspid heart valve. Methods of loading a delivery device and delivering an implant are also disclosed.

22 Claims, 7 Drawing Sheets

(51) Int. Cl.
*A61F 2/962* (2013.01)
*A61F 2/966* (2013.01)

(52) U.S. Cl.
CPC .... *A61F 2/9661* (2020.05); *A61F 2002/9623* (2020.05); *A61F 2002/9665* (2013.01)

(58) Field of Classification Search
CPC ............ A61F 2002/9665; A61F 2/2439; A61F 2/2442; A61F 2/2466
See application file for complete search history.

(56) References Cited

U.S. PATENT DOCUMENTS

| | | | |
|---|---|---|---|
| 9,517,337 B2 | 12/2016 | Ollivier | |
| 9,884,185 B2 | 2/2018 | Ollivier | |
| 10,258,468 B2 | 4/2019 | Deem et al. | |
| 10,376,364 B2 | 8/2019 | Tamir et al. | |
| 10,575,950 B2 | 3/2020 | McLean | |
| 10,687,969 B2 | 6/2020 | Folan et al. | |
| 2009/0318947 A1 | 12/2009 | Garcia et al. | |
| 2011/0264203 A1 | 10/2011 | Dwork et al. | |
| 2011/0276121 A1 | 11/2011 | Levine | |
| 2013/0231735 A1* | 9/2013 | Deem | A61F 2/2436 623/2.11 |
| 2014/0012369 A1 | 1/2014 | Murry, III et al. | |
| 2014/0200649 A1 | 7/2014 | Essinger et al. | |
| 2014/0214046 A1 | 7/2014 | Puckett | |
| 2015/0374492 A1 | 12/2015 | Alkhatib | |
| 2017/0128205 A1 | 5/2017 | Tamir et al. | |
| 2019/0008636 A1 | 1/2019 | Francis et al. | |
| 2020/0069422 A1 | 3/2020 | Essinger et al. | |

OTHER PUBLICATIONS

Culp et al., "Relative Ultrasonographic Echogenicity of Standard, Dimpled, and Polymeric-Coated Needles," JVIR, vol. 11, No. 3, pp. 351-358 (Mar. 2000).

\* cited by examiner

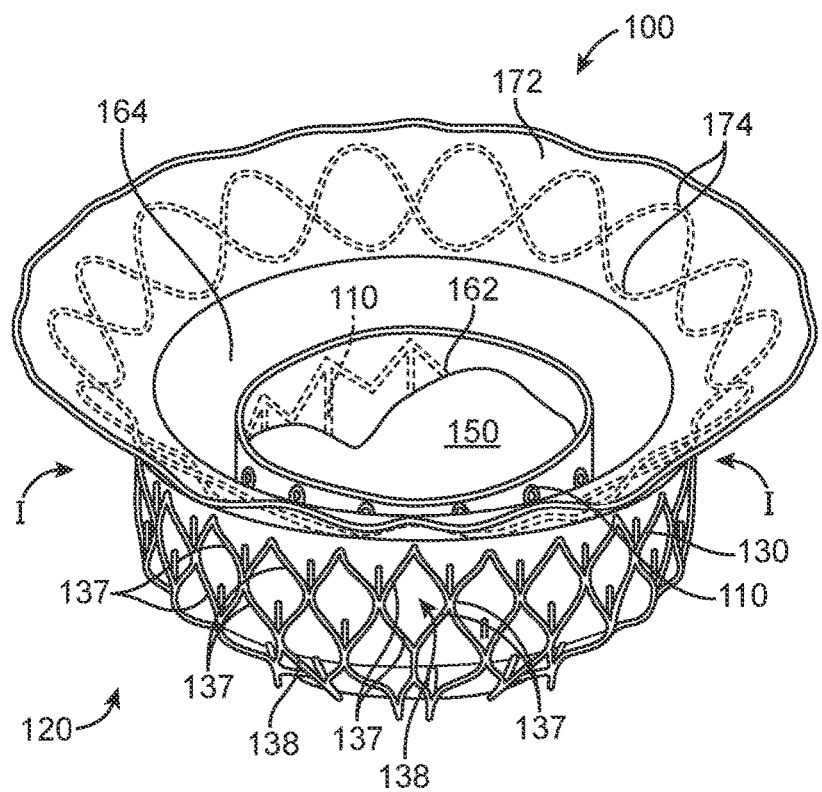
FIG. 1A
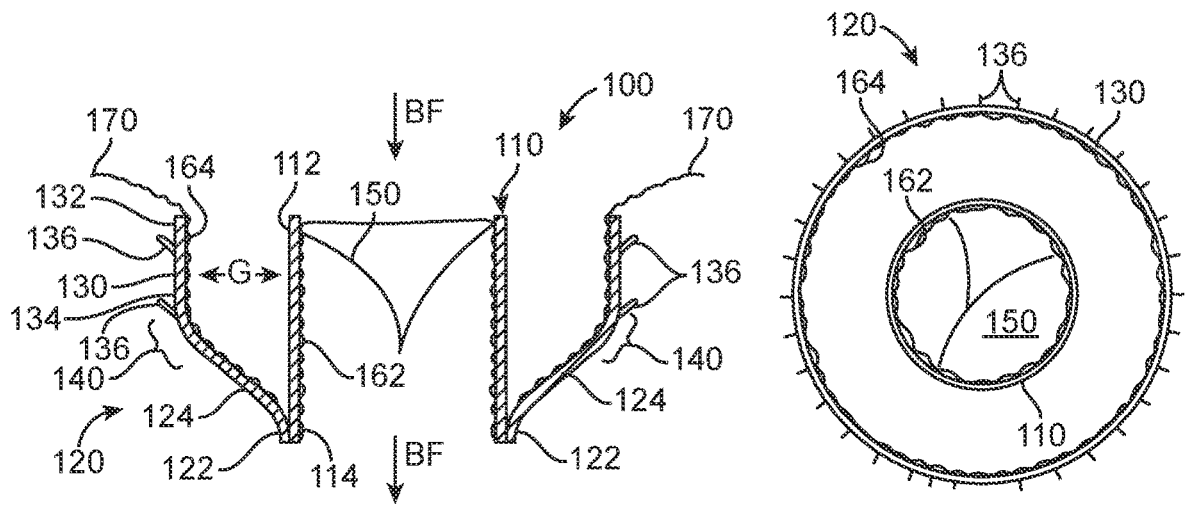
FIG. 1B
FIG. 1C

BIASED CAPSULE FOR TRANSCATHETER VALVE REPAIR AND METHODS

CROSS-REFERENCE TO RELATED APPLICATIONS

This Non-Provisional Patent Application claims the benefit of the filing date of U.S. Provisional Patent Application Ser. No. 63/157,202, filed Mar. 5, 2021, entitled "BIASED CAPSULE FOR TRANSCATHETER VALVE REPAIR AND METHODS," the entire teachings of which are incorporated herein by reference.

FIELD

The present technology is generally related to delivery devices and methods for transcatheter delivery and deployment of a prosthesis to a heart valve.

BACKGROUND

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of a prosthetic heart valve or prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped arrangement, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place.

The present disclosure addresses problems and limitations associated with the related art.

SUMMARY

The techniques of this disclosure generally relate to delivery devices and methods for transcatheter delivery and deployment of a prosthesis, such as a prosthetic heart valve, to a defective heart valve. Aspects of the disclosure are particularly beneficial for transcatheter edge-to-edge tricuspid repair as various delivery devices are configured to reduce the depth in which the device needs to be inserted into the right ventricle during delivery of the prosthesis. Access to a tricuspid valve can be challenging in that existing implanted devices may be in the anatomy, reducing the space available for the delivery device. In addition, visualization of the delivery system and implant may be challenging as metallic capsules can cause artifacts due to density. Further, chordae, papillary muscles serve as obstacles for delivery and the right ventricle is generally shorter than the left ventricle. All of these considerations result in a general desire for a delivery device capable of delivering an implant to a tricuspid valve while reducing a length the delivery device extends into the right ventricle. Aspects of the disclosure are also suitable for the delivery of other cardiovascular implants or gastrointestinal stents, for example.

In one aspect, the present disclosure provides a delivery device including a handle assembly and a piston mount having a distal portion. The distal portion includes a stop extending radially from and fixed to the distal portion. Additionally, the delivery device includes a capsule assembly including a helical compression spring and a plurality of retraction members secured about a distal end of the compression spring. Tensioning of the retraction members compresses the compression spring against the stop.

In another aspect, the disclosure provides methods including providing a delivery device including a handle assembly, a piston mount connected to the handle assembly and having a distal portion terminating at a nose cap. The distal portion includes a stop extending radially from and fixed to the distal portion. The delivery device further includes a capsule assembly including a biasing element and a plurality of retraction members secured about a distal end of the biasing element. An implant is compressed onto the piston mount and within the capsule assembly. The method further includes delivering the implant to a heart valve with the delivery device and tensioning the retraction members to collapse the biasing element against the stop to partially unsheathe the implant. In addition, the method includes distally advancing the nose cap to fully unsheathe the implant and release the implant from the delivery device. Aspects of the discourse also include methods of loading an implant to a delivery device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1A is a top isometric view of a prosthetic heart valve in an expanded arrangement.

FIG. 1B is a cross-sectional side view of the prosthetic heart valve of FIG. 1A.

FIG. 1C is a top view schematically illustrating the prosthetic heart valve of FIGS. 1A-1B.

DETAILED DESCRIPTION

Figure 2:
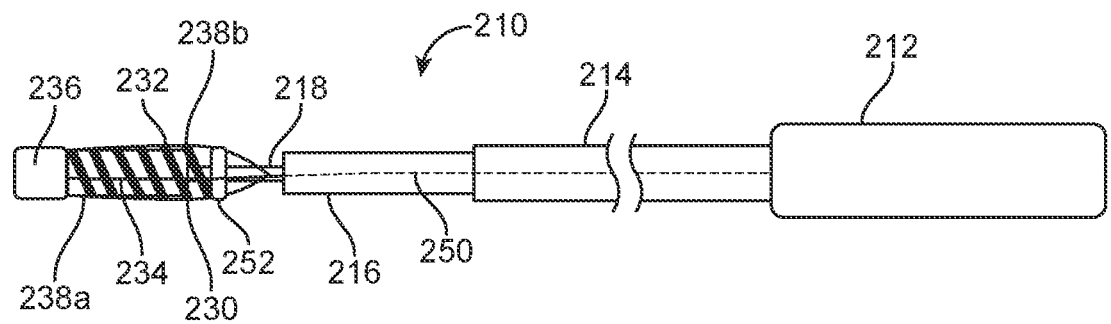
FIG. 2 is a schematic illustration of a delivery device.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

As referred to herein, implants, stented prostheses, stented prosthetic heart valves or "prosthetic valves" useful with the various systems, devices and methods of the present disclosure may assume a wide variety of configurations. Stented prosthetic heart valves can include, for example, a bioprosthetic heart valve having tissue leaflets or a synthetic heart valve having polymeric, metallic or tissue-engineered leaflets, and can be specifically configured for replacing valves of the human heart. The prosthetic valves and stented prostheses of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having an uncompressed, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol). The stent frame can be laser-cut from a single piece of material, or can be assembled from a number of discrete components.

One non-limiting example of a stented prosthesis or implant 100 suitable for use with systems and devices of the disclosure is illustrated in FIGS. 1A-1C. In this example, the implant is a prosthetic heart valve 100 includes a valve support 110, an anchoring member 120 attached to the valve support 110, and a prosthetic valve assembly 150 within the valve support 110. Referring in particular to FIG. 1B, the valve support 110 has an inflow region 112 and an outflow region 114. The prosthetic valve assembly 150 is arranged within the valve support 110 to allow blood to flow from the inflow region 112 through the outflow region 114 (arrows BF), but prevent blood from flowing in a direction from the outflow region 114 through the inflow region 112.

The anchoring member 120 includes a base 122 attached to the outflow region 114 of the valve support 110 and a plurality of arms 124 projecting laterally outward from the base 122. The anchoring member 120 also includes a fixation structure 130 extending from the arms 124. The fixation structure 130 can include a first portion 132 and a second portion 134. The first portion 132 of the fixation structure 130, for example, can be an upstream region of the fixation structure 130 that, in a deployed configuration as shown in FIG. 1B, is spaced laterally outward apart from the inflow region 112 of the valve support 110 by a gap G. The second portion 134 of the fixation structure 130 can be a downstream-most portion of the fixation structure 130. The fixation structure 130 can be a cylindrical ring (e.g., straight cylinder or conical), and the outer surface of the fixation structure 130 can define an annular engagement surface configured to press outwardly against the native heart valve annulus. The fixation structure 130 can further include a plurality of fixation elements 136 that project radially outward and are inclined toward an upstream direction. The fixation elements 136, for example, can be barbs, hooks, or other elements that are inclined only in the upstream direction (e.g., a direction extending away from the downstream portion of the implant 100).

The anchoring member 120 has a smooth bend 140 between the arms 124 and the fixation structure 130. For example, the second portion 134 of the fixation structure 130 extends from the arms 124 at the smooth bend 140. The arms 124 and the fixation structure 130 can be formed integrally from a continuous strut or support element such that the smooth bend 140 is a bent portion of the continuous strut. In other examples, the smooth bend 140 can be a separate component with respect to either the arms 124 or the fixation structure 130. For example, the smooth bend 140 can be attached to the arms 124 and/or the fixation structure 130 using a weld, adhesive or other technique that forms a smooth connection. The smooth bend 140 is configured such that the implant 100 can be recaptured in a capsule or other container after the implant 100 has been at least partially deployed.

The implant 100 can further include a first sealing member 162 on the valve support 110 and a second sealing member 164 on the anchoring member 120. The first and second sealing members 162, 164 can be made from a flexible material, such as a polymeric material. The first sealing member 162 can cover the interior and/or exterior surfaces of the valve support 110. The first sealing member 162 is attached to the interior surface of the valve support 110, and the prosthetic valve assembly 150 is attached to the first sealing member 162 and commissure portions of the valve support 110. The second sealing member 164 is attached to the inner surface of the anchoring member 120. As a result, the outer annular engagement surface of the fixation structure 130 is not covered by the second sealing member 164 so that the outer annular engagement surface of the fixation structure 130 directly contacts the tissue of the native annulus.

The implant 100 can further include an extension member or brim 170. The extension member 170 can be an extension of the second sealing member 164, or it can be a separate component attached to the second sealing member 164 and/or the first portion 132 of the fixation structure 130. The extension member 170 can be a flexible member that, in a deployed state as shown in FIGS. 1A-1B, flexes relative to the first portion 132 of the fixation structure 130. In operation, the extension member 170 guides the implant 100 during implantation such that the device is located at a desired elevation and centered relative to the native annulus. In some embodiments, one or more components of the extension member 170 can be made of or include a radiopaque material.

As best shown in FIG. 1A, valve support 110 defines a first frame (e.g., an inner frame) and fixation structure 130 of the anchoring member 120 defines a second frame (e.g., an outer frame) that each include a plurality of structural elements. The fixation structure 130, more specifically, includes structural elements 137 arranged in diamond-shaped cells 138 that together form at least a substantially cylindrical ring when freely and fully expanded as shown in FIG. 1A. The structural elements 137 can be struts or other structural features formed from metal, polymers, or other suitable materials that can self-expand or be expanded by a balloon or other type of mechanical expander.

The fixation structure 130 can be a generally cylindrical fixation ring having an outwardly facing engagement surface. For example, in the example shown in FIG. 1A, the outer surfaces of the structural elements 137 define an annular engagement surface configured to press outwardly against the native annulus in the deployed state. In a fully expanded state without any restrictions, the fixation structure 130 is at least substantially parallel to the valve support 110. However, the fixation structure 130 can flex inwardly (arrow I) in the deployed state when it presses radially outwardly against the inner surface of the native annulus of a heart valve.

The first sealing member 162 lines the interior surface of the valve support 110, and the second sealing member 164 along the inner surface of the fixation structure 130. The extension member 170 has a flexible web 172 (e.g., a fabric) and a support member 174 (e.g., metal or polymeric strands) attached to the flexible web 172. The flexible web 172 can extend from the second sealing member 164 without a metal-to-metal connection between the fixation structure 130 and the support member 174. For example, the extension member 170 can be a continuation of the material of the second sealing member 164. Several embodiments of the extension member 170 are thus a floppy structure that can readily flex with respect to the fixation structure 130. The support member 174 can have a variety of configurations and be made from a variety of materials, such as a double-serpentine structure made from Nitinol. Additional details regarding the implant 100 can be found in U.S. patent Ser. No. 15/643,011, the disclosure of which is hereby incorporated by reference.

In one example, the implant 100 has a diameter of 48 mm in the expanded arrangement for delivery within a 35 French capsule or the like. In another example, the implant 100 has a diameter of 42 mm in the expanded arrangement.

Figure 3:
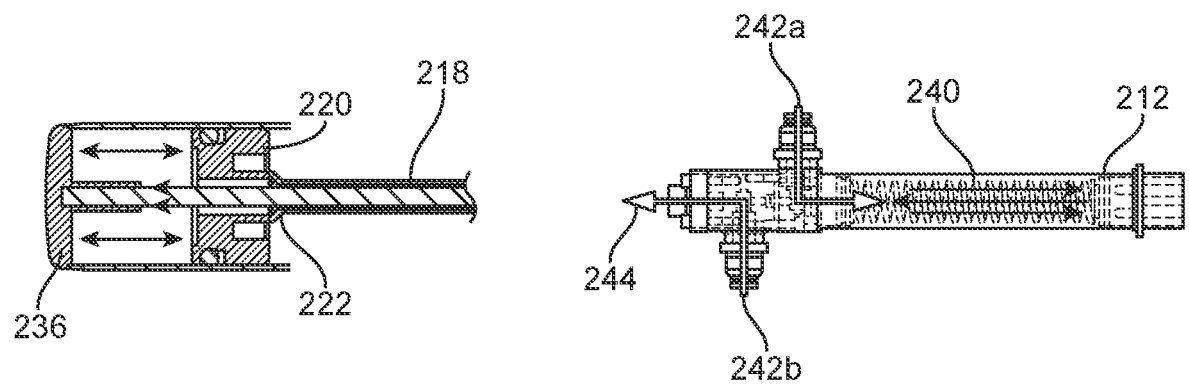
FIG. 3 is a schematic illustration of the delivery device of FIG. 2.

Referring now in addition to FIGS. 2-3, which illustrate select components of a delivery device 210 suitable for transcatheter delivery of an implant or prosthesis, such as that of FIGS. 1A-1C. In general terms, the delivery device 210 includes a handle assembly 212 supporting an optional outer sheath 214 and an inner catheter 216. Provided within the inner catheter 216 is a piston mount 218 supporting a piston or valve retainer 220 (not visible) within nose cap 236 that is of any of the type known in the art for releasably retaining an implant compressed within a catheter or the like. The piston mount 218 can be an elongated shaft or catheter, for example. Over a distal end 222 of piston mount 218, a capsule assembly 230 is provided that is configured to transition from a loaded arrangement in which the capsule assembly 230 compressively sheathes the implant to a partially-deployed arrangement in which the capsule assembly is at least partially withdrawn from the implant, to a deployed arrangement in which the implant is fully unsheathed from the capsule assembly so that the implant can expand, releasing the implant from the piston and the delivery device 210. In various embodiments of the disclosure, the capsule assembly 230 includes a biasing element 232 that is a helical compression spring and two or more retraction wires 234 secured to the biasing element 232 and extending proximally for tensioning to correspondingly pull the biasing element against its bias to unsheathe the implant 100. At the distal end 222 of the piston mount 218, distal to the capsule assembly 230, a nose cap 236 can be provided. In some embodiments, the capsule assembly 230 may at least partially be positioned within the nose cap 236 in the loaded arrangement (FIG. 2) and in other examples, the capsule assembly 230 may merely abut or otherwise terminate proximal to the nose cap 236 in the loaded arrangement. In non-limiting examples, the nose cap 236 can have a length of about 20 mm (+10 mm/−15 mm), which greatly minimizes a depth in which the delivery device 210 needs to be deployed into the right ventricle during a transcatheter tricuspid replacement procedure and can reduce anatomical interactions, particularly for small and/or curved right ventricles. In some examples, the nose cap 236 is tapered in a distal direction.

Actuation of the retraction members 234 can be mechanically accomplished by tensioning the retraction members 234. In another example, the retraction wires 234 can be tensioned using a first fluid path 240 connected to a first fluid source 242a as is depicted in FIG. 3, which can also be configured to recapture the implant 100 within the capsule assembly 230. With one hydraulically driven device 210, once implant position is finalized within the patient anatomy, fluid from a second inflation device or connection 242b is injected into a second fluid path 244 configured to deploy the implant 100 by releasing the implant from the piston/valve retainer 220. Fluid is directed through the second fluid path 244 into the nose cap 236 to push the nose cap distally into the ventricle, for example, releasing the implant 100 from the delivery device 210 and allowing for full deployment of the implant. It is further envisioned that tensioning of the retraction members 234 can be pneumatically or mechanically achieved.

Figure 4A:
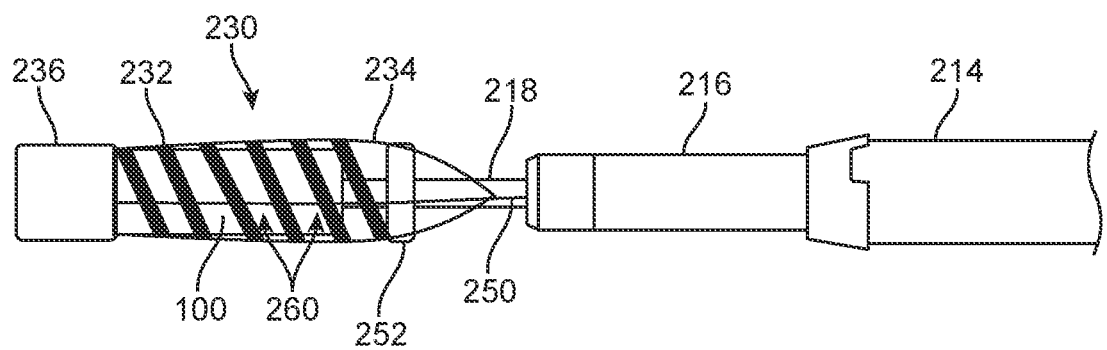
FIG. 4A is a schematic illustration of a distal end of the device of FIGS. 2-3 in a loaded arrangement.
Figure 4B:
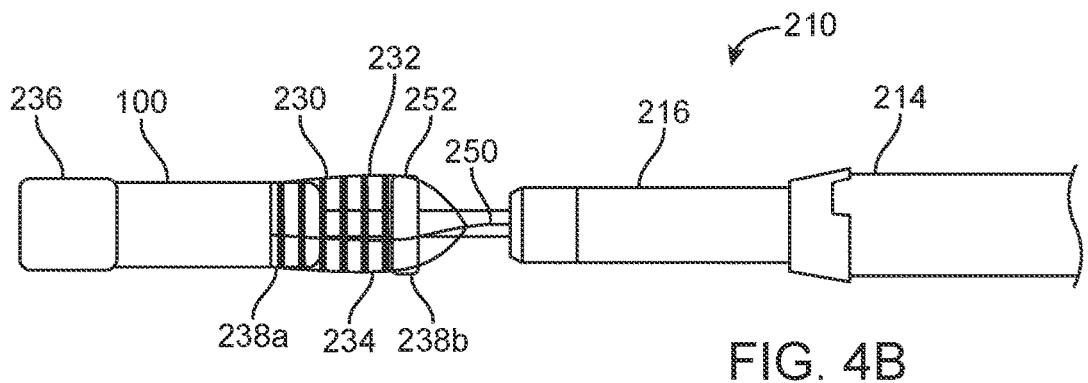
FIGS. 4B-4D are schematic illustrations of the delivery device of FIG. 4A in a partially deployed arrangement.
Figure 4C:
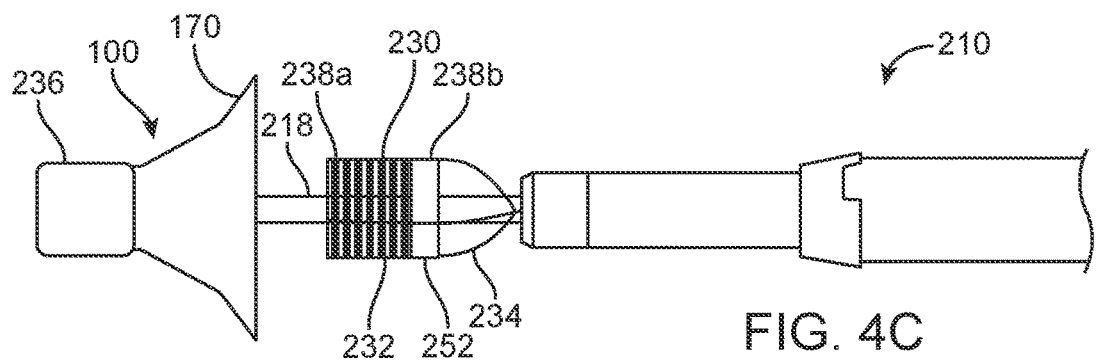
Figure 4D:
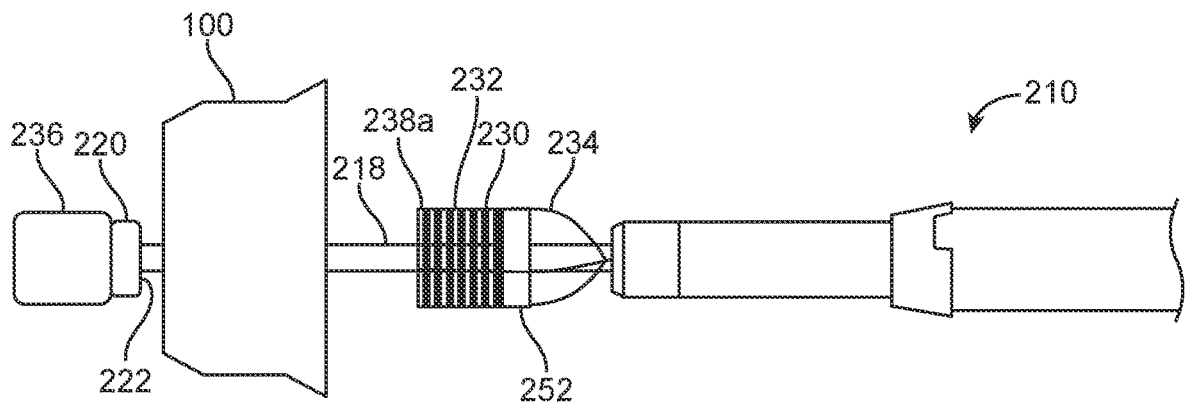
Figure 4E:
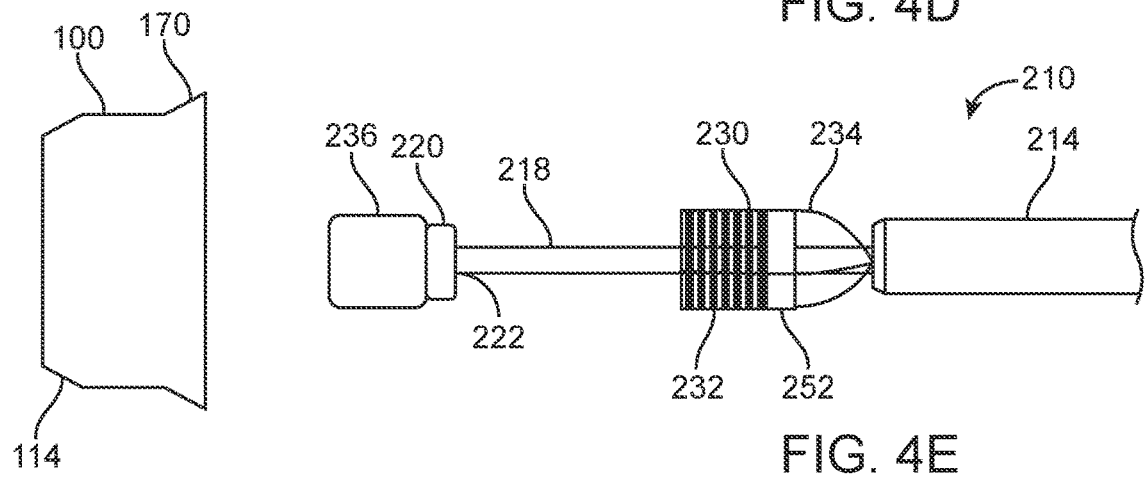
FIG. 4E is a schematic illustration of the delivery device of FIGS. 2-4D in a deployed arrangement

The capsule assembly 230 can take many forms. Referring in addition to FIGS. 4A-4C, which illustrate the piston mount 218 supporting an implant (e.g., implant 100) compressed thereon and retained with the piston 220 (not visible). In one example, the capsule assembly 230 includes the biasing element 232 being a helical compression spring or the like, that is biased against compression of the biasing element. The plurality of elongated retraction members 234 (generally referenced) are secured to the biasing element 232 via any suitable method including, but not limited to, welding or crimping. In the illustrated example, four retraction members 234 are provided although not all retraction members are visible in the drawings. In other examples, between 2-6 retraction members 234 are provided. Each retraction member 234 can be a wire, cord, filament or the like. In one example, the retraction members 234 are approximately equally spaced (+/−5 degrees). Each retraction member 234 is secured to the biasing element 232, at a distal end 238a of the biasing element 232. In one example, the retraction members 234 are brought together or joined at a proximal end 238b of the biasing element 232. The retraction members 234 or elongated member 250 interconnecting the retraction members 234 extends proximally to the handle assembly 212 for tensioning to transition the capsule assembly 230 from the loaded arrangement to the deployed arrangement. Proximal movement and tensioning of the retraction members 234 correspondingly pulls the biasing element 232 proximally to compress the biasing member 232 and unsheathe the implant 100 for expansion and deployment in the process as is generally shown in FIGS. 4A-4E.

Figure 5:
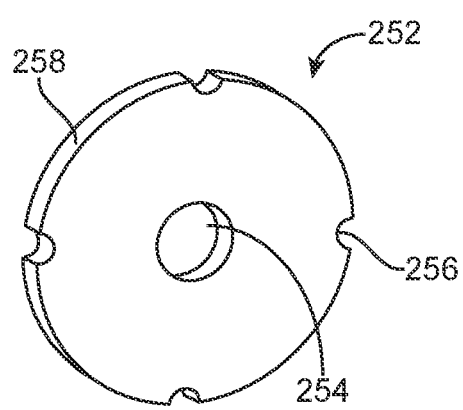
FIG. 5 illustrates a stop of the delivery device of FIGS. 2-4E.
Figure 6:
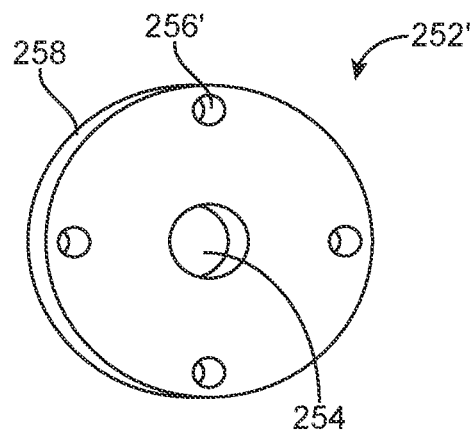
FIG. 6 illustrates an alternate stop.

In one embodiment, the piston mount 218 includes a stop 252 that is secured to the piston mount 218 and extends radially therefrom. In one example, the stop 252 is positioned between the biasing element 232 and the inner catheter 214. The stop 252 is configured to restrict movement of the biasing element 232 proximally past the stop 252. In this way, the stop 252 can be made of a metal or rigid polymer, for example. The stop 252 can be one of many configurations suitable for this purpose. In the example of FIG. 5, the stop 252 can include a central aperture 254 through which the piston mount 218 can be threaded and notches or grooves 256 within a periphery surface 258 of the stop 252 in which one respective retraction member 234 can be positioned. In the example, if FIG. 6, an alternate stop 252' can include apertures 256' provided through a thickness of the stop through which the retraction members 234 extend as they are tensioned. Alternatively, if the retraction members 234 are joined as shown in FIG. 4A, for example, one or more apertures can be provided in the stop to receive the elongated member 250. It will be understood that the number and placement of notches and apertures can vary depending on the number and orientation of the retraction members provided.

The biasing element 232 of the disclosure can take many configurations. Generally, the biasing member 232 can include any structure that biases both the capsule assembly 230 against compression along a length of the capsule assembly. Therefore, the biasing element 232 has a natural arrangement in which the biasing element is not exposed to external forces and a compressed arrangement in which the biasing element is compressed against its bias to reduce its length as compared to the natural arrangement. In one example, the biasing element 232 is a helical compression spring formed of a round wire or a flat wire that is about 1.5 mm thick (+/−1 mm) so that any cleat/feature protrusion of the implant (typically between 0.5 mm-1.5 mm) would be within the profile of the spring wire of the helical compression spring biasing element 232 when the implant 100 is compressed within the biasing element 232. In one example, the biasing element 232 has a length of about 25 mm (+/−5 mm) in the natural arrangement to fully cover the atrial and intra-annular segments of the implant 100, assuming the implant has approximately a 17 mm intra-annular frame and 10 mm brim 170 length in the compressed arrangement. Further wire forming the biasing element 232 can be radiused to be atraumatic to the anatomy and the implant 100. In various examples, a pitch of the wire forming a biasing element 232 can be set to hold the implant 100 in a compressed configuration until the implant 100 is deployed while maintaining gaps 260 (generally referenced in FIG. 4A) between wraps 262 (generally referenced in FIG. 4A) to allow for visualization during the procedure and lessens echogenic shadowing under ultrasound as compared to a denser metal capsule design. In one example, the gap 260 between wraps 262 is at least equivalent to the width of the wire and up to 10 mm when the biasing element 232 is in a natural arrangement. In various examples, any metal components of the delivery device 210, such as the biasing element 232, can include a dimpled or otherwise textured surface to provide echogenic attributes. The present inventors have found that gaps 260 formed between wraps 262 of the helical compression spring are beneficial in that they provide enhanced visualization of the capsule assembly 230 as compared to metallic sheath capsules that are more likely to cause artifacts due to their metallic density.

Figure 7:
FIG. 7 is a schematic illustration of the implant of FIGS. 1A-1C.
Figure 8:
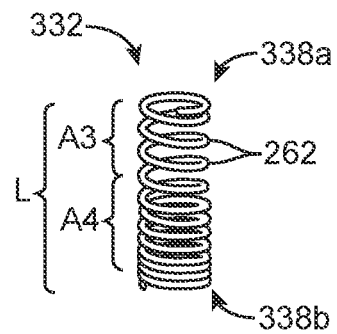
FIGS. 8-9 are perspective views of biasing elements that can be utilized with the delivery device of FIGS. 2-4E, which are specifically configured for the implant of FIG. 7.
Figure 9:
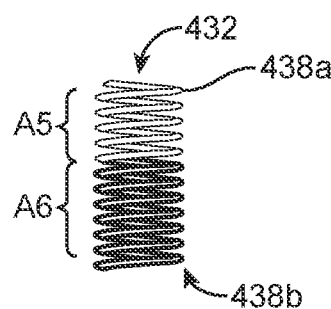

Referring now in addition to FIGS. 7-9, the biasing element 232 can optionally be configured specifically to accommodate attributes of the particular implant to be delivered. For example, if the implant 100 (FIG. 7) has a lower outwardly radial force at an area A1 at its proximal end or brim 170 as compared to an area A2 at the distal, outflow region 114 of the implant 100, a biasing element 332 can optionally have the corresponding attributes of FIG. 8. For example, a proximal end 338a of the biasing element 332 may have an area A3 having a lower pitch as compared to an area A4 a distal end 338b of the biasing element. As shown in FIG. 9, an area A5 at a proximal end 438a of biasing element 432 can be made of a thinner wire as compared to an area A6 at a distal end 438b of the biasing element 432. Other illustrative examples include a biasing element having varying pitch, filar count, material composition or wire thickness, for example. The respective transition points for changes in pitch, filar count, material composition or wire thickness can correspond to transition points along a length L of the implant 100 when the implant is in the compressed arrangement. It will be understood that biasing elements of the disclosure can be modified to suit other particular implant forces in a similar manner. Further, it is to be understood that the features of all of the biasing elements disclosed herein are combinable and interchangeable.

Figure 10:
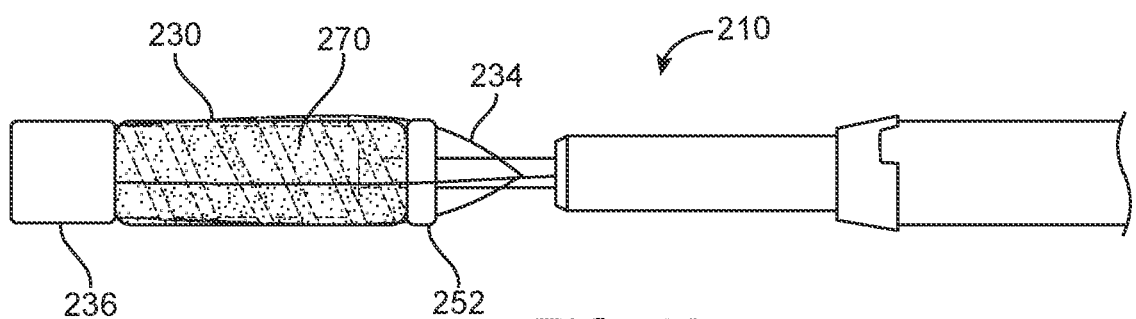
FIG. 10 is a schematic illustration of a capsule assembly including a sheath that can be utilized with the delivery device of FIGS. 2-4E.

Referring now in addition to FIG. 10, in various embodiments of the disclosure, the capsule assembly 230 can optionally include a sleeve 270 covering the biasing element 232. A few non-limiting examples of materials suitable for the sleeve 270 include thermoplastic polyurethanes or polyether block amide 25/30. The sleeve 270 is beneficial in that it can protect the anatomy from implant 100 features until the implant is ready for deployment. In such an embodiment, the biasing element 232 holds the implant 100 in a crimped configuration until deployment while maintaining gaps 260 between helical spring wraps 262 to allow for visualization of the capsule assembly 230 during deployment of the implant 100.

Figure 11A:
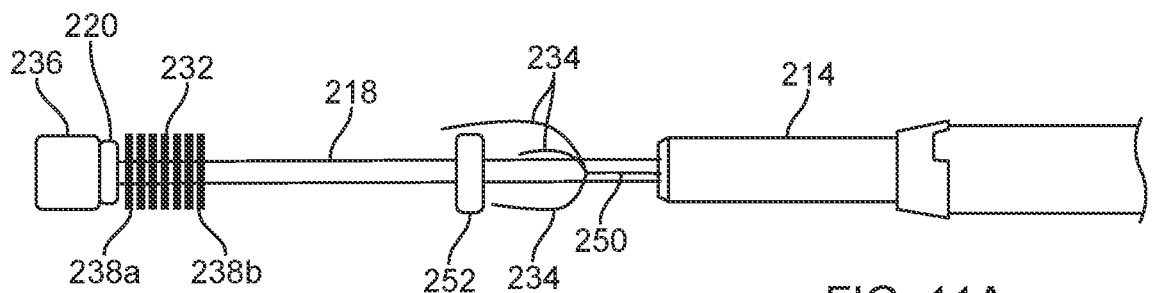
FIGS. 11A-11E schematically illustrate one method of loading an implant to the delivery device of FIGS. 2-4E.
Figure 11B:
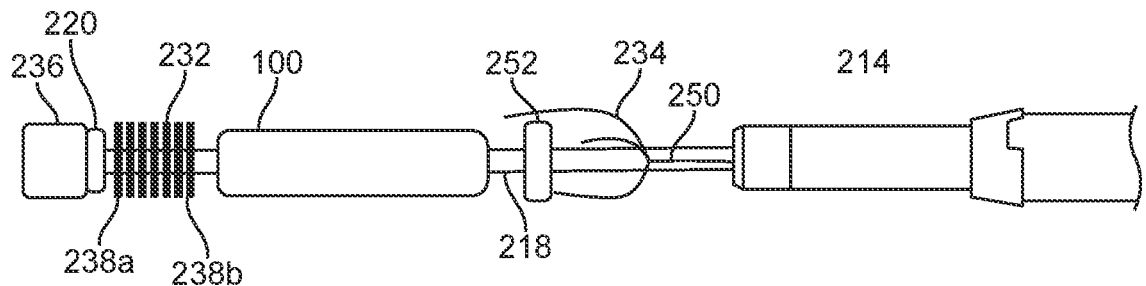
Figure 11C:
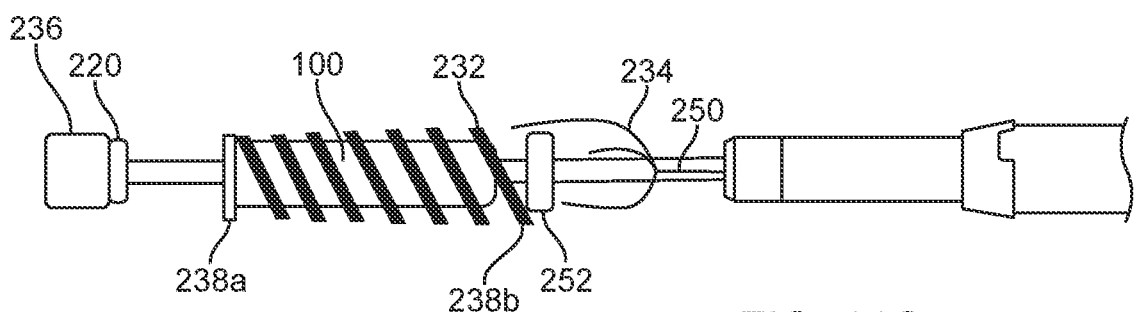
Figure 11D:
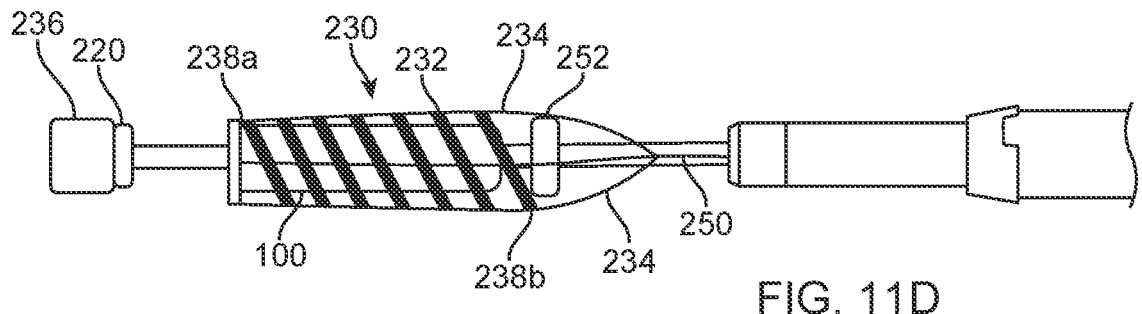
Figure 11E:
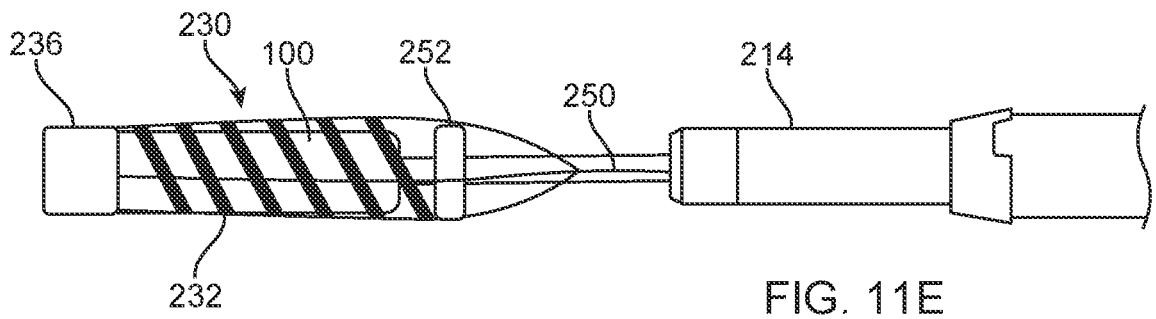

Referring now in addition to FIGS. 11A-11E, which illustrate one method of loading an implant (e.g., implant 100) to the delivery device 210 of FIGS. 2-4E. In this example, the biasing element 232 is positioned and compressed such that both distal and proximal ends 238a, 238b of the biasing element 232 are adjacent the nose cap 236 (FIG. 11A). Then, the implant 100 is loaded over the piston mount 218 and crimped to compress the implant using any known technique (FIG. 11B). In one example, the implant 100 is loaded onto piston 220 (see also, FIG. 2). Next, compression of the biasing element 232 is released at a controlled rate to allow the biasing element to expand and sheathe the implant 100. In some methods, at least part of the capsule assembly 230 remains in the nose cap 236 as the biasing element 232 is allowed to expand. If the implant 100 includes cleats, the biasing element 232 is released in the same direction as the cleats to prevent snagging (FIG. 11C). Then, the retraction wires 234 can be attached to the distal end 238a of the biasing element 232 (FIG. 11D). If applicable, piston 220 can be then be fixed to any implant retention features (e.g., T-bars or the like as known in the art) and the nose cap 236 can be moved proximally to lock the implant 100 in place, compressed within the capsule assembly 230 (FIG. 11E). Optionally, the nose cap 236 can be moved proximally to at least partially cover the capsule assembly 230, including covering one or more of the biasing element 232, one or more retraction members 234 and/or any sleeve 270.

Figure 12:
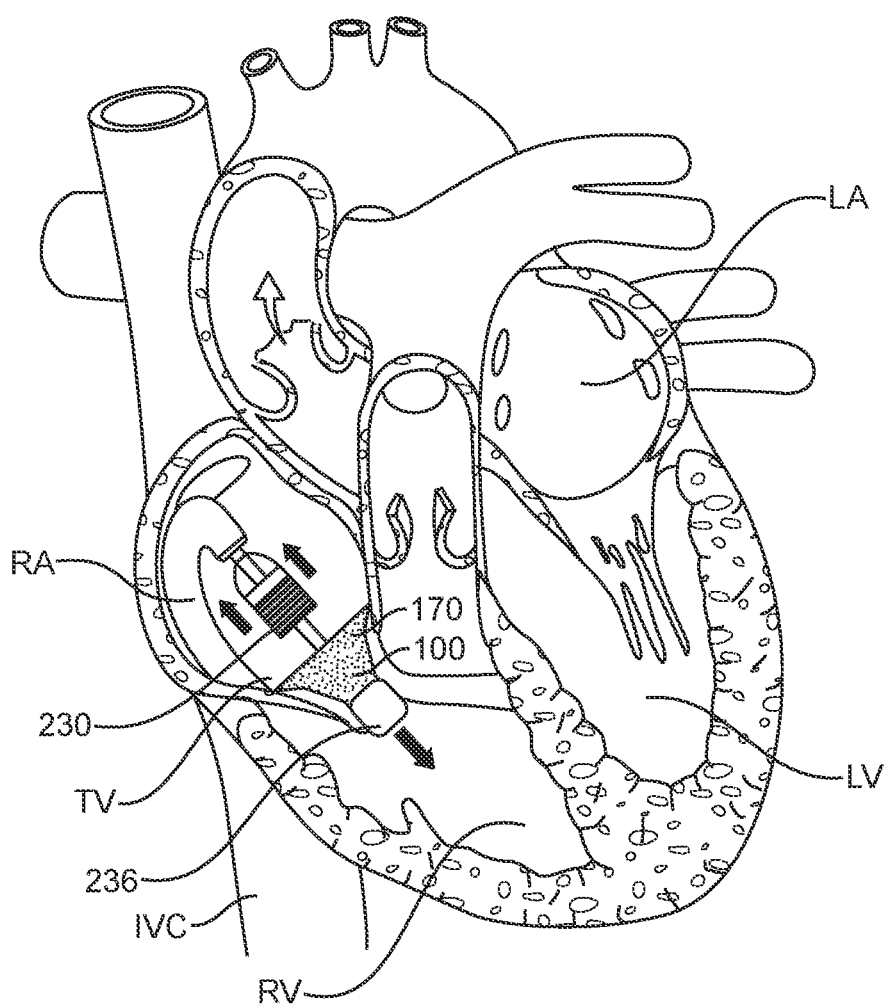
FIG. 12 is a schematic illustration of a method of delivery of an implant to a tricuspid valve with a delivery device of the disclosure.

Referring in addition now to FIG. 12, which schematically illustrates one method of the disclosure. In this example, an implant (e.g., implant 100) is crimped and loaded onto the piston mount 218 of the delivery device 210 having the capsule assembly 230 sheathing the implant 100 as shown in FIG. 11E. The physician then advances the delivery device 210 via transcatheter procedure from the interior vena cava IVC into the right atrium RA of a patient's heart. The nose cap 236 can optionally be connected to steering components, as used in the art, used to steer the nose cap during delivery. The nose cap 236 can be steered through the tricuspid valve annulus TV until the compressed, loaded implant 100 is within the tricuspid valve annulus TV. Proper positioning of the implant 100 in the right atrium RA, proximal to the annulus TV can be confirmed via imaging techniques. Once the physician navigates the implant 100 to the desired position, the implant 100 can be transitioned to a partially expanded arrangement by proximally withdrawing and compressing the distal end 238a of the biasing element 232 against the stop 252 by tensioning the retraction members 234. Partial, unsheathing of the implant 100 will cause the proximal end or brim 170 of the implant 100 to expand outwardly. Optionally, the biasing element 232 position can be monitored via fluoroscopy. If desired, tension in the retraction members 234 can be lessened to at least partially recapture the implant 100 within the capsule assembly 230 for recovery or repositioning of the implant 100, as desired. When the implant 100 is in the desired location, the nose cap 236 can be advanced distally via actuation at the handle assembly 212, thereby freeing the implant 100 from the piston 220 and delivery device 210. The implant 100 is then fully seated in the patient's anatomy. The nose cap 236 and piston mount 218 can be proximally retracted through the implant 100 and the delivery system can be withdrawn from the patient in the same manner as delivered.

In methods where the implant is a replacement tricuspid valve and the implantation site is a tricuspid valve, only the nose cap will be deployed into the right ventricle (a length of about 10-20 mm), which is generally a 50-75% reduction in depth that the device deploys into the right ventricle as compared to a traditional sheath capsule, which can have a length of about 41 mm. Due to the reduction in right ventricle deployment depth, devices of the disclosure are suitable for a wider number of patient anatomies. In addition, the smaller, tapered nose cap reduces the risk of anatomical interactions, which are more common with tricuspid valve replacement procedures.

Figure 13:
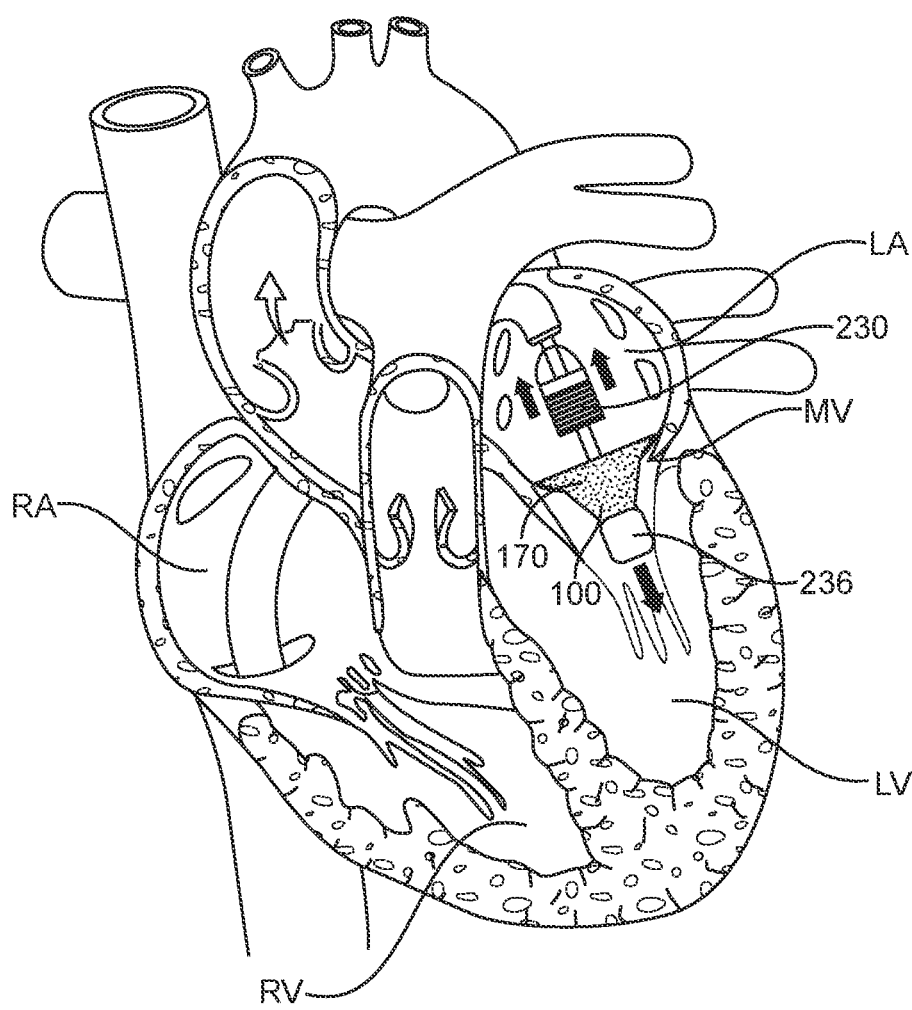
FIG. 13 is a schematic illustration of a method of delivery of an implant to a mitral valve with a delivery device of the disclosure.

Referring in addition now to FIG. 13, which schematically illustrates another method of the disclosure. In this example, an implant (e.g., implant 100) is crimped and loaded onto the piston mount 218 of the delivery device 210 having the capsule assembly 230 sheathing the implant 100 as shown in FIG. 11E. The physician then advances the delivery device 210 via transcatheter procedure into the left atrium LA of a patient's heart. The nose cap 236 can optionally be connected to steering components, as used in the art, used to steer the nose cap during delivery. The nose cap 236 can be steered through a mitral valve annulus MV until the compressed, loaded implant 100 is within the mitral valve annulus MV. Proper positioning of the implant 100 in the left atrium LA, proximal to the annulus MV can be confirmed via imaging techniques. Once the physician navigates the implant 100 to the desired position, the implant 100 can be transitioned to a partially expanded arrangement by proximally withdrawing and compressing the distal end 238a of the biasing element 232 against the stop 252 by tensioning the retraction members 234. Partial, unsheathing of the implant 100 will cause the proximal end or brim 170 of the implant 100 to expand outwardly. Optionally, the biasing element 232 position can be monitored via fluoroscopy. If desired, tension in the retraction members 234 can be lessened to at least partially recapture the implant 100 within the capsule assembly 230 for recovery or repositioning of the implant 100, as desired. When the implant 100 is in the desired location, the nose cap 236 can be advanced distally via actuation at the handle assembly 212, thereby freeing the implant 100 from the piston 220 and delivery device 210. The implant 100 is then fully seated in the patient's anatomy. The nose cap 236 and piston mount 218 can be proximally retracted through the implant 100 and the delivery system can be withdrawn from the patient in the same manner as delivered. In one example, only the nose cap 236 is advanced into the left ventricle LV during the procedure as the capsule assembly 230 will remain in the left atrium. In one example, the delivery device does not extend further than 30 mm into a left ventricle adjacent the mitral valve during the release of the implant.

It is envisioned that devices and methods of the disclosure are suitable for many types of cardiovascular procedures including mitral valve replacement, tricuspid valve replacement, aortic valve replacement, pulmonic valve replacement, aortic valve replacement, aortic aneurysm stent grafts, peripheral vascular stents. It is further envisioned that devices and methods of the disclosure are suitable for the delivery of gastrointestinal stents, for example.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A delivery device comprising:
   a handle assembly;
   a piston mount having a distal portion, the distal portion including a stop extending radially from and fixed to the distal portion; and
   a capsule assembly including a helical compression spring and a plurality of retraction members secured about a distal end of the compression spring, the compression spring being disposed over the piston mount and being configured to receive a prosthesis between the piston mount and the compression spring;
   wherein tensioning of the retraction members compresses the compression spring against the stop.

2. The delivery device of claim 1, further comprising a nose cap at least partially positioned distal to the compression spring.

3. The delivery device of claim 2, wherein the delivery device includes a loaded arrangement in which the compression spring is positioned within the nose cap.

4. The delivery device of claim 1, wherein the capsule assembly includes a sleeve coupled to the compression spring, the sleeve configured to compress with the compression spring.

5. The delivery device of claim 1, wherein the compression spring has a varying pitch along a length of the compression spring.

6. The delivery device of claim 1, wherein the compression spring has a varying thickness along a length of the compression spring.

7. The delivery device of claim 1, wherein the compression spring has a varying filar count along a length of the compression spring.

8. The delivery device of claim 1, wherein the compression spring has a varying material composition along a length of the compression spring.

9. The delivery device of claim 1, further comprising a prosthesis positioned within the compression spring in a loaded arrangement.

10. The delivery device of claim 1, wherein the stop includes grooves within a periphery of the stop in which the retraction members are positioned.

11. The delivery device of claim 1, wherein the stop includes an inner aperture to receive the piston mount and includes a plurality of outer apertures in which the retraction members are positioned.

12. The delivery device of claim 2, further comprising:
    a piston coupled to a distal end of the piston mount; and
    a fluid chamber defined within the nose cap and distal of the piston, wherein the fluid chamber is configured to receive fluid to push the nose cap distally.

13. The delivery device of claim 12, wherein the piston is configured to be coupled to the prosthesis.

14. A method comprising:
    delivering an implant to a native heart valve with a delivery device, the delivery device including:
      a handle assembly;
      a piston mount connected to the handle assembly and having a distal portion terminating at a nose cap, the distal portion including a stop extending radially from and fixed to the distal portion, and
      a capsule assembly including a biasing element and a plurality of retraction members secured about a distal end of the biasing element; wherein the implant is compressed onto the piston mount and within the biasing element;
    tensioning the retraction members to collapse the biasing element against the stop to partially unsheathe the implant; and
    distally advancing the nose cap to fully unsheathe the implant and release the implant from the delivery device.

15. The method of claim 14, wherein the heart valve is an atrioventricular valve.

16. The method of claim 15, wherein the delivery device does not extend further than 30 mm into a ventricle adjacent the atrioventricular valve during the release of the implant.

17. The method of claim 15, wherein the capsule assembly remains in an atrium adjacent the atrioventricular valve as the implant is partially and fully unsheathed.

18. The method of claim 14, wherein the biasing element is a helical compression spring.

19. The method of claim 18, wherein the capsule assembly includes a sleeve coupled to the compression spring, wherein the sleeve collapses with the compression spring.

20. The method of claim 14, wherein the biasing element is positioned underneath the nose cap during the step of delivering the implant.

21. The method of claim 15, wherein the atrioventricular valve is a mitral valve.

22. A delivery device comprising:
    a handle assembly;
    a piston mount having a distal portion, the distal portion including a stop extending radially from and fixed to the distal portion; and
    a capsule assembly including a biasing member and a plurality of retraction members secured about a distal end of the compression spring, the biasing member being disposed over the piston mount and being configured to receive a prosthesis between the piston mount and the biasing member;
    wherein tensioning of the retraction members compresses the biasing member against the stop.

* * * * *